(12) United States Patent
Thibault et al.

(10) Patent No.: US 11,955,228 B2
(45) Date of Patent: Apr. 9, 2024

(54) METHODS AND SYSTEM FOR SIMULATED RADIOLOGY STUDIES BASED ON PRIOR IMAGING DATA

(71) Applicant: GE Precision Healthcare LLC, Wauwatosa, WI (US)

(72) Inventors: Jean-Baptiste Thibault, Brookfield, WI (US); Jonathan S. Maltz, Oakland, CA (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 188 days.

(21) Appl. No.: 17/643,738

(22) Filed: Dec. 10, 2021

(65) Prior Publication Data

US 2023/0187054 A1    Jun. 15, 2023

(51) Int. Cl.
| | | |
|---|---|---|
| G06T 17/00 | (2006.01) | |
| A61B 6/46 | (2024.01) | |
| G16H 30/40 | (2018.01) | |
| G16H 50/50 | (2018.01) | |
| G16H 50/70 | (2018.01) | |

(52) U.S. Cl.
CPC ............ *G16H 30/40* (2018.01); *A61B 6/465* (2013.01); *A61B 6/466* (2013.01); *G06T 17/00* (2013.01); *G16H 50/50* (2018.01); *G16H 50/70* (2018.01); *G06T 2200/24* (2013.01); *G06T 2210/41* (2013.01)

(58) Field of Classification Search
CPC ......... G06T 11/008; G06T 2207/20081; G06T 2207/10081; G06T 7/0012; G06T 2200/24; G06T 2207/10072; G06T 2207/30004; G06T 19/20; G06T 11/003; G06T 17/00; G06T 2210/41; G06T 2200/04; G06T 2200/08; G16H 30/40; G16H 50/50; G16H 30/20
See application file for complete search history.

(56) References Cited

U.S. PATENT DOCUMENTS

| | | | |
|---|---|---|---|
| 8,744,867 | B2 | 6/2014 | Spertus |
| 9,471,987 | B2 | 10/2016 | Harder et al. |
| 9,875,339 | B2 | 1/2018 | Namer Yelin et al. |
| 10,346,974 | B2 | 7/2019 | Sloan et al. |

(Continued)

FOREIGN PATENT DOCUMENTS

| | | |
|---|---|---|
| WO | 2017153122 A1 | 9/2017 |
| WO | 2021038002 A1 | 3/2021 |
| WO | 2021229223 A1 | 11/2021 |

OTHER PUBLICATIONS

Abadi, E. et al., "Virtual clinical trials in medical imaging: a review," Journal of Medical Imaging, vol. 7, No. 4, Jul. 2020, Available Online Apr. 11, 2020, 41 pages.

(Continued)

*Primary Examiner* — Hau H Nguyen
(74) *Attorney, Agent, or Firm* — McCoy Russell LLP (57) ABSTRACT

Systems and methods are provided for simulating medical images based on previously acquired data and a defined imaging protocol. In an example, a method includes generating a simulated medical image of a patient via virtual imaging based on previously obtained medical images and a scan intent of the virtual imaging, and outputting an imaging protocol based on a virtual protocol of the virtual imaging.

19 Claims, 5 Drawing Sheets

(56) References Cited

U.S. PATENT DOCUMENTS

| | | |
|---|---|---|
| 10,803,354 B2 | 10/2020 | Zhao et al. |
| 2010/0183206 A1 | 7/2010 | Carlsen et al. |
| 2020/0218922 A1* | 7/2020 | Chen .................... A61B 6/4417 |
| 2023/0019873 A1* | 1/2023 | Landon ..................... G06T 7/75 |

OTHER PUBLICATIONS

AV/ Ben-Cohen et al: "Virtual PET Images from CT Data Using Deep Convolutional Networks: Initial Results", arxiv.org, Cornell University Library, 201 Olin Library Cornell University Ithaca, NY 14853, Jul. 30, 2017(Jul. 30, 2017), XP081279081, DOI: 10.1007/978-3-319-68127-6 6.

EP application 22210115.6 filed Nov. 29, 2022—extended Search Report dated Apr. 13, 2023; 9 pages.

* cited by examiner

METHODS AND SYSTEM FOR SIMULATED RADIOLOGY STUDIES BASED ON PRIOR IMAGING DATA

FIELD

Embodiments of the subject matter disclosed herein relate to medical imaging, and more specifically to predicting radiology images.

BACKGROUND

Radiology is a branch of medicine that uses imaging to view the internal structures of a patient or object without performing an invasive procedure on the patient or object. Examples of such imaging modalities may include x-ray radiography, computed tomography (CT), positron emission tomography (PET), fluoroscopy, ultrasound, and magnetic resonance imaging (MRI). As one example, a CT scan uses the differential transmission of x-rays through a target volume to acquire image data and to construct tomographic images (e.g., three-dimensional representations of the interior of the human body).

A radiologist or radiological technologist may select an imaging protocol, including the imaging modality and parameters for a scan, based on a diagnostic task or desired imaging outcome. However, it may be difficult to predict the likely appearance of the resulting images, which may result in repeated scans. As another example, radiologists or radiological technologists may be slow to implement new imaging system capabilities or protocols due to being unable to predict the imaging outcome.

BRIEF DESCRIPTION

In one aspect, a method comprises generating a simulated medical image of a patient via virtual imaging based on previously obtained medical images and a scan intent of the virtual imaging, and outputting an imaging protocol based on a virtual protocol of the virtual imaging.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Embodiments of the present disclosure will now be described, by way of example, with reference to the FIGS. 1-6, which relate to various embodiments for simulating radiology studies based on previously acquired imaging data. Currently, imaging system users may not have a defined process for fine-tuning protocol selection based on an imaging task at hand. As a result, the selection of a specific protocol and parameters may be a matter of experience. When new imaging equipment is introduced into a clinic, it may take time for users to learn the capabilities of the equipment and the performance of specific protocols.

Thus, according to embodiments disclosed herein, simulated radiology studies may be performed based on an imaging intent, in order to more efficiently and accurately optimize image acquisition settings. As a result, the imaging may be performed with optimal use of the capabilities of a particular imaging system for performance of a specific diagnostic or interventional task. In this way, an occurrence of suboptimal or unusable studies may be reduced, which may in turn accelerate user training, increase an imaging throughput, and reduce a dose of radiation, contrast, and/or radiotracer to patients from unusable/repeated studies. Further, a diagnostic quality of the images may be increased by using the simulated radiology studies to optimize image acquisition settings, reducing an amount of time until a diagnosis is made while decreasing a mental burden on a provider. Overall, both provider and patient satisfaction may be increased.

Figure 1:
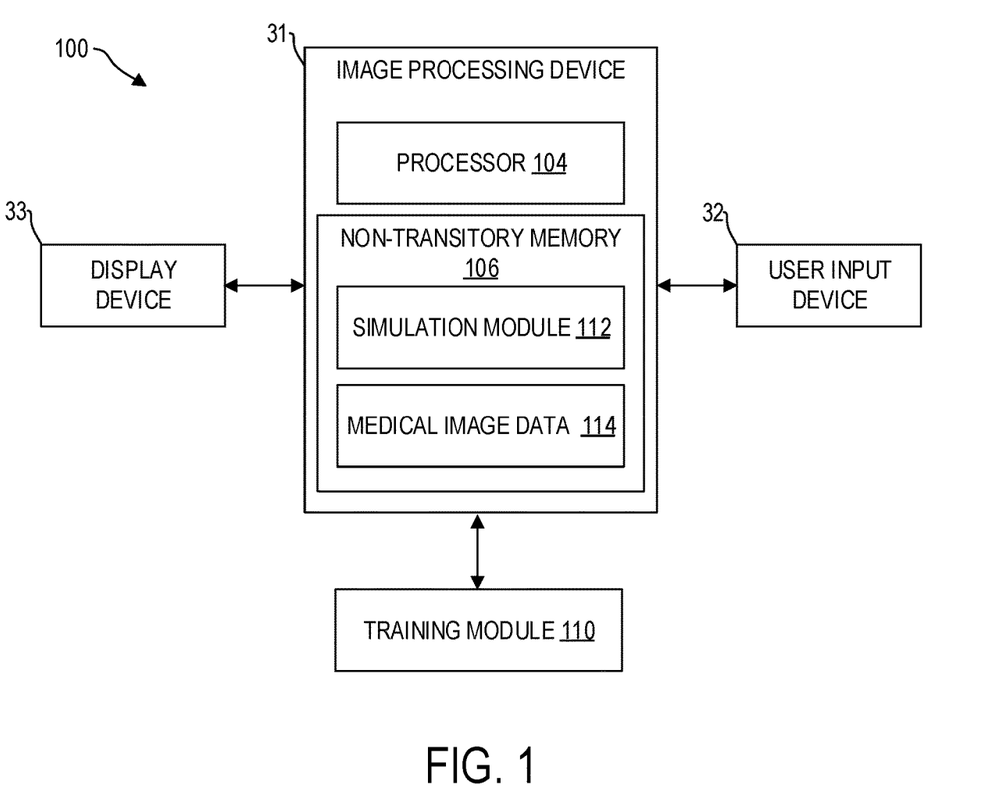
FIG. 1 is a schematic diagram illustrating an image processing system, according to an embodiment.
Figure 3:
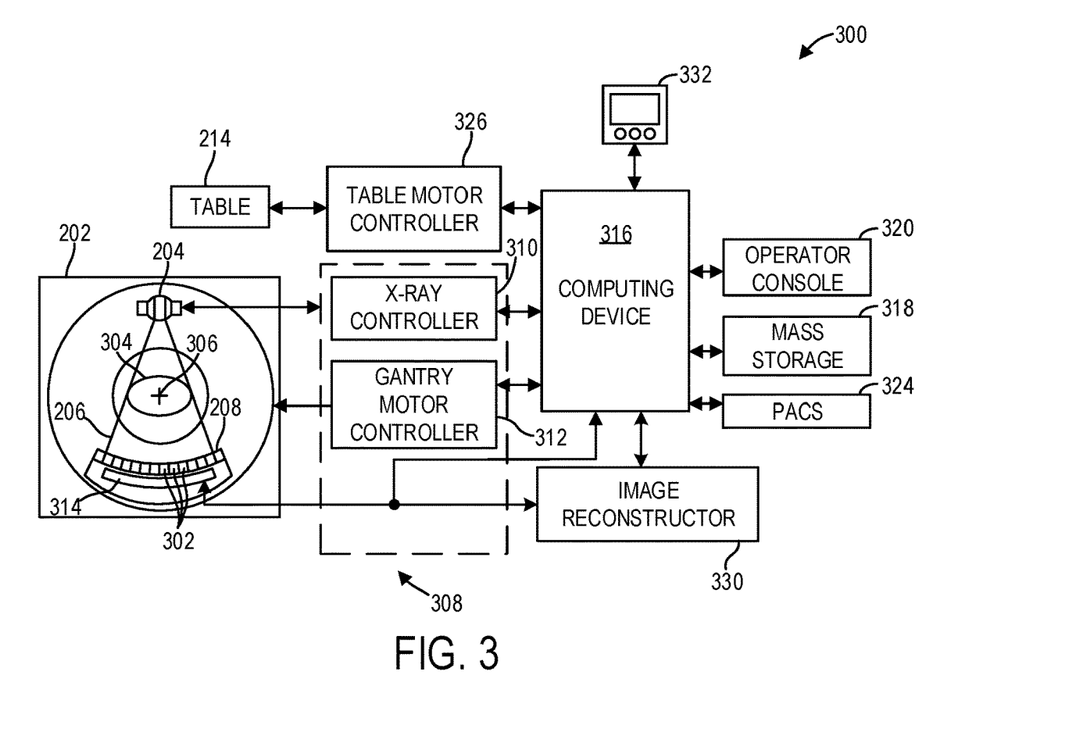
FIG. 3 shows a block schematic diagram of an exemplary imaging system, according to an embodiment.
Figure 4:
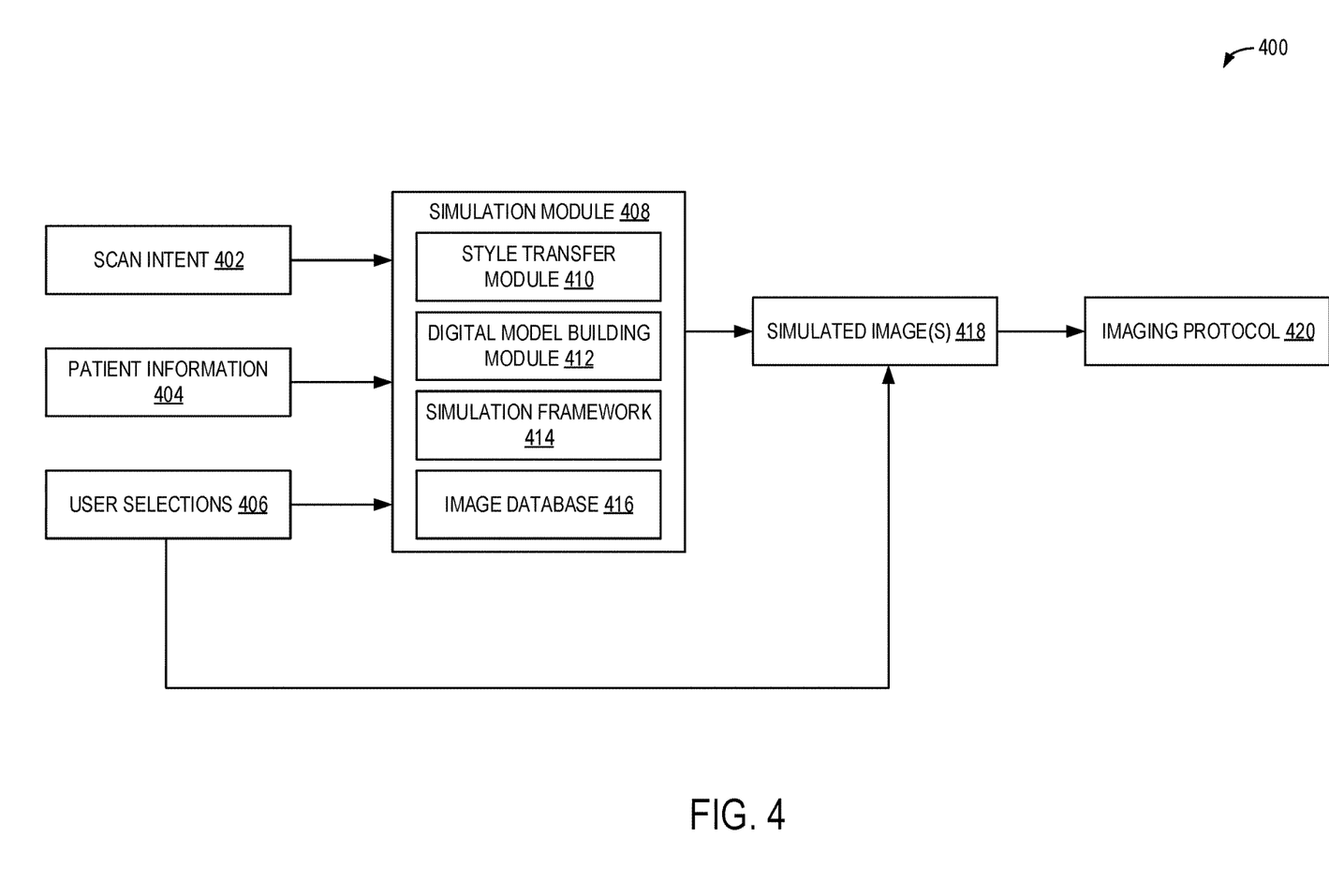
FIG. 4 shows a block diagram of an exemplary workflow for simulating medical images via virtual imaging, according to an embodiment.
Figure 5:
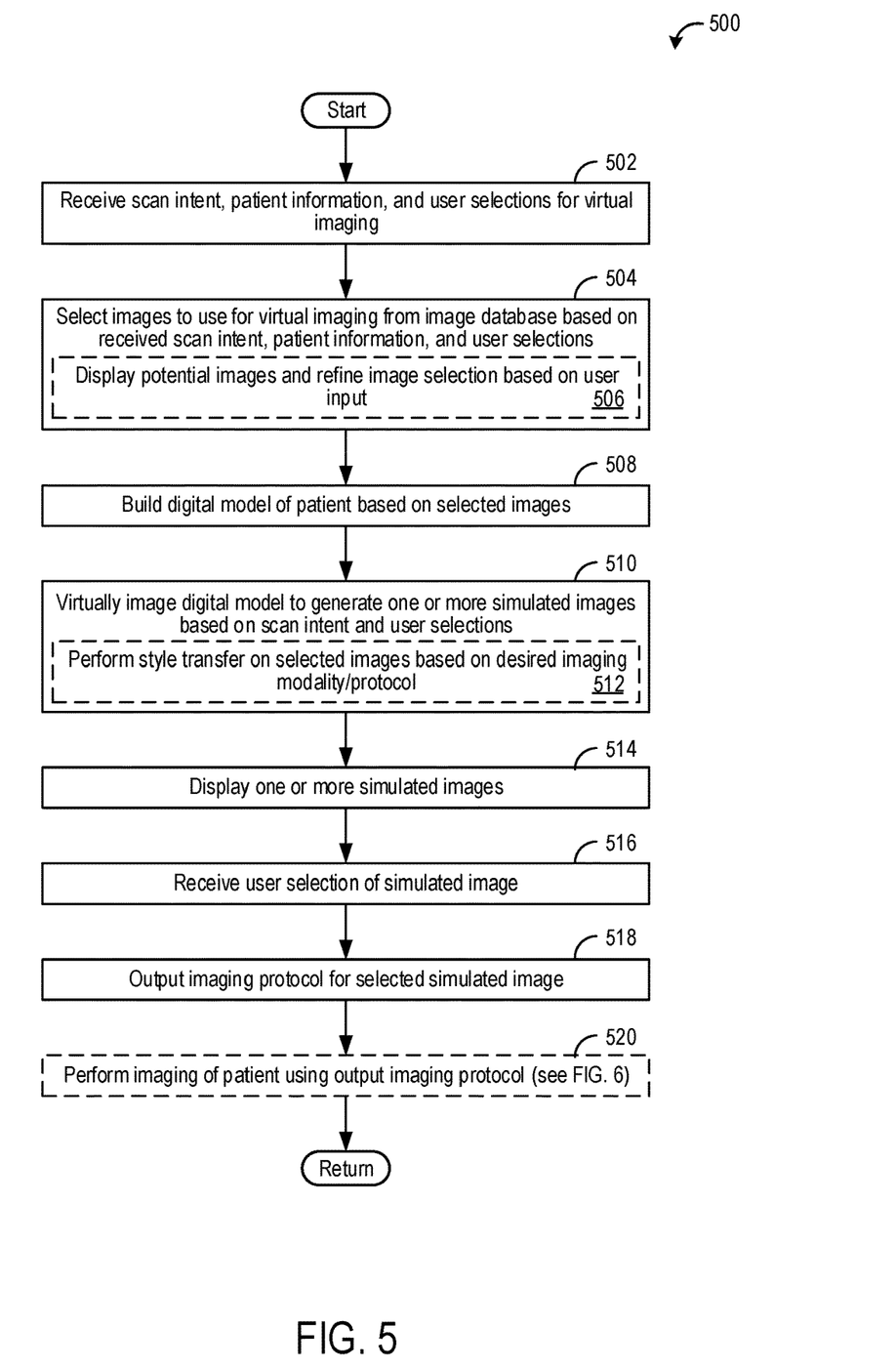
FIG. 5 is a flow chart of an exemplary method for simulating medical images based on prior imaging data, according to an embodiment.

FIG. 1 shows an exemplary image processing system that may be used to simulate medical images via virtual imaging, such as using the workflow shown in FIG. 4 and according to the method of FIG. 5. An imaging system, such as the CT imaging system shown in FIGS. 2 and 3, may be used to generate images that are retrieved from an image database via the image processing system of FIG. 1 for use in simulating the medical images. Further, the CT imaging system may be used to generate new medical images using protocols generated via the virtual imaging, such as according to the method of FIG. 6. It may be understood that although the CT imaging system is shown by way of example, other imaging modalities may be used without departing from the scope of this disclosure.

Referring to FIG. 1, an example image processing system 100 is shown. In some embodiments, the image processing system 100 is incorporated into a medical imaging system, such as a magnetic resonance imaging (MRI) system, a computed tomography (CT) system, a single-photon emission computed tomography (SPECT) system, etc. In some embodiments, at least a portion of the image processing system 100 is disposed at a device (e.g., an edge device or server) communicably coupled to the medical imaging system via wired and/or wireless connections. In some embodiments, the image processing system 100 is disposed at a separate device (e.g., a workstation) that can receive images from the medical imaging system or from a storage device that stores the images generated by the medical imaging system. The image processing system 100 may comprise an image processing device 31, a user input device 32, and a display device 33. For example, the image processing device 31 may be operatively/communicatively coupled to the user input device 32 and the display device 33.

The image processing device 31 includes a processor 104 configured to execute machine readable instructions stored in a non-transitory memory 106. The processor 104 may be single core or multi-core, and the programs executed by processor 104 may be configured for parallel or distributed processing. In some embodiments, the processor 104 may optionally include individual components that are distributed throughout two or more devices, which may be remotely located and/or configured for coordinated processing. In some embodiments, one or more aspects of the processor 104 may be virtualized and executed by remotely-accessible networked computing devices configured in a cloud computing configuration. In some embodiments, the processor 104 may include other electronic components capable of carrying out processing functions, such as a digital signal processor, a field-programmable gate array (FPGA), or a graphic board. In some embodiments, the processor 104 may include multiple electronic components capable of carrying out processing functions. For example, the processor 104 may include two or more electronic components selected from a plurality of possible electronic components, including a central processor, a digital signal processor, a field-programmable gate array, and a graphics board. In still further embodiments, the processor 104 may be configured as a graphical processing unit (GPU), including parallel computing architecture and parallel processing capabilities.

The non-transitory memory 106 may store a simulation module 112 and medical image data 114. The simulation module 112 may include one or more machine learning models, such as deep learning networks, comprising a plurality of weights and biases, activation functions, loss functions, gradient descent algorithms, and instructions for implementing the one or more deep neural networks to process input medical images and patient data and output a simulated medical image. For example, the simulation module 112 may store instructions for implementing one or more deep learning methods that perform image synthesis and style transfer. The simulation module 112 may include trained and/or untrained neural networks and may further include training routines, or parameters (e.g., weights and biases), associated with one or more deep learning methods (e.g., machine learning models). The simulation module 112 may also include physics-based models, such as Monte Carlo simulation, analytic simulation, finite element models, Boltzmann transport models, raytracing models, and so forth. These physics-based models may be used in conjunction with trained models, and the parameters of these physics-based models may themselves be learned.

The image processing device 31 may be communicatively coupled to a training module 110, which includes instructions for training one or more of the deep learning methods stored in the simulation module 112. The training module 110 may include instructions that, when executed by the processor 104, cause the processor 104 to perform training of the simulation module 112. In one example, the training module 110 includes instructions for receiving training data sets from the medical image data 114, which comprise sets of medical images, associated ground truth labels/images, and associated model outputs for use in training one or more of the deep learning methods stored in the simulation module 112. The training module 110 may receive medical images, associated ground truth labels/images, and associated model outputs for use in training the one or more machine learning models from sources other than the medical image data 114, such as other image processing systems, the cloud, etc. In some embodiments, one or more aspects of the training module 110 may include remotely-accessible networked storage devices configured in a cloud computing configuration. Further, in some embodiments, the training module 110 is included in the non-transitory memory 106. Additionally or alternatively, in some embodiments, the training module 110 may be used to generate the simulation module 112 offline and remote from the image processing system 100. In such embodiments, the training module 110 may not be included in the image processing system 100 but may generate data stored in the image processing system 100.

The non-transitory memory 106 further stores the medical image data 114. The medical image data 114 includes, for example, functional imaging images captured by a functional imaging modality, such as SPECT and PET systems, anatomical images captured by an MRI system or a CT system, etc. For example, the medical image data 114 may include initial and follow-up medical scan images stored in the non-transitory memory 106. In some embodiments, the non-transitory memory 106 may include components disposed at two or more devices, which may be remotely located and/or configured for coordinated processing. In some embodiments, one or more aspects of the non-transitory memory 106 may include remotely-accessible networked storage devices in a cloud computing configuration.

The image processing system 100 may further include the user input device 32. The user input device 32 may comprise one or more of a touchscreen, a keyboard, a mouse, a trackpad, a motion sensing camera, or another device configured to enable a user to interact with and manipulate data within the image processing device 31. As an example, the user input device 32 may enable a user to analyze and rank imaged structures.

The display device 33 may include one or more display devices utilizing any type of display technology. In some embodiments, the display device 33 may comprise a computer monitor and may display unprocessed images, processed images, simulated images, parametric maps, and/or exam reports. The display device 33 may be combined with the processor 104, the non-transitory memory 106, and/or the user input device 32 in a shared enclosure or may be a peripheral display device. The display device 33 may include a monitor, a touchscreen, a projector, or another type of display device, which may enable a user to view medical images and/or interact with various data stored in the non-transitory memory 106.

It may be understood that the image processing system 100 shown in FIG. 1 is one non-limiting embodiment of an image processing system, and other image processing systems may include more, fewer, or different components without parting from the scope of this disclosure.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

Figure 2:
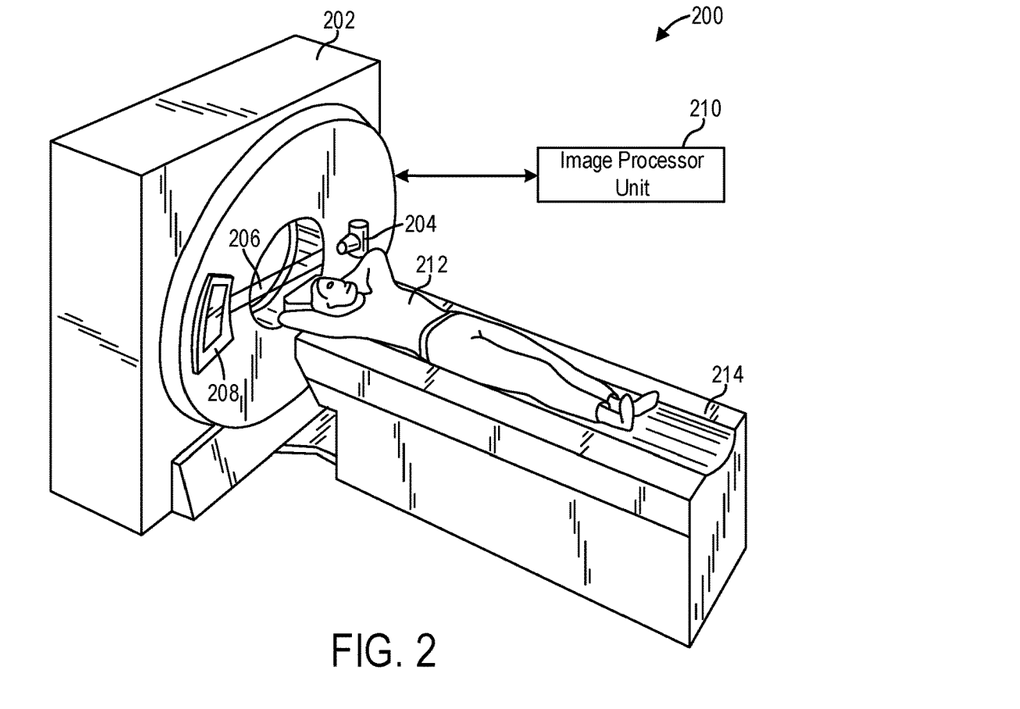
FIG. 2 shows a pictorial view of an imaging system that may utilize an image processing system, such as image processing system of FIG. 1, according to an embodiment.

FIG. 2 illustrates an exemplary CT system 200 configured for CT imaging. Particularly, the CT system 200 is configured to image a subject 212, such as a patient, an inanimate object, an in vitro tissue sample, one or more manufactured parts, and/or foreign objects such as dental implants, stents, and/or contrast agents present within the body. The CT system 200 may be used to generate medical images processed by the image processing system 100 of FIG. 1, for example, although other imaging modalities are also possible (e.g., MRI, PET, SPECT, and so forth). In one embodiment, the CT system 200 includes a gantry 202, which, in turn, may include at least one x-ray source 204 configured to project a beam of x-ray radiation 206 for use in imaging the subject 212 laying on a table 214. Specifically, the x-ray source 204 is configured to project the x-ray radiation 206 toward a detector array 208 positioned on the opposite side of the gantry 202. Although FIG. 2 depicts only a single x-ray source 204, in certain embodiments, multiple x-ray sources and detectors may be employed to project a plurality of x-ray radiation beams 206 for acquiring projection data at different energy levels corresponding to the patient. In some embodiments, the x-ray source 204 may enable dual- or multi-energy imaging by kilovoltage (kVp) switching. In some embodiments, the x-ray detector array 208 is a photon-counting detector, which is capable of differentiating x-ray photons of different energies. In other embodiments, two sets of x-ray sources and detectors are used to generate dual-energy projections, with one set at low-kVp and the other at high-kVp. It should thus be appreciated that the methods described herein may be implemented with single energy acquisition techniques as well as dual- or multi-energy acquisition techniques.

In certain embodiments, the CT system 200 further includes an image processor unit 210 configured to reconstruct images of a target volume of the subject 212 using an iterative or analytic image reconstruction method. For example, the image processor unit 210 may use an analytic image reconstruction approach, such as filtered back projection (FBP), to reconstruct images of a target volume of the subject 212. As another example, the image processor unit 210 may use an iterative image reconstruction approach, such as advanced statistical iterative reconstruction (ASIR), conjugate gradient (CG), maximum likelihood expectation maximization (MLEM), model-based iterative reconstruction (MBIR), and so on, to reconstruct images of a target volume of the subject 212. As described further herein, in some examples, the image processor unit 210 may use both an analytic image reconstruction approach such as FBP in addition to an iterative image reconstruction approach. In some examples, the image processor unit 210 may be included as a part of or communicatively coupled to the image processing device 31 of FIG. 1.

In some configurations of the CT system 200, the x-ray source 204 projects a cone-shaped x-ray radiation beam, which is collimated to lie within an X-Y-Z plane of a Cartesian coordinate system and generally referred to as an "imaging plane." The x-ray radiation beam 206 passes through an object being imaged, such as the subject 212. The x-ray radiation beam 206, after being attenuated by the object, impinges upon an array of detector elements at the detector array 208. The intensity of the attenuated x-ray radiation beam received at the detector array 208 is dependent upon the attenuation of the x-ray radiation beam by the object. Each detector element of the array produces a separate electrical signal that is a measurement of the x-ray beam attenuation at the detector location. The attenuation measurements from all the detector elements are acquired separately to produce a transmission profile.

In some configurations of the CT system 200, the x-ray source 204 and the detector array 208 are rotated with the gantry 202 within the imaging plane and around the object to be imaged such that an angle at which the x-ray radiation beam 206 intersects the object constantly changes. A group of x-ray radiation attenuation measurements, e.g., projection data, from the detector array 208 at one gantry angle is referred to as a "view." A "scan" of the object includes a set of views made at different gantry angles, or view angles, during at least a partial revolution of the x-ray source and detector. It is contemplated that the benefits of the methods described herein accrue to medical imaging modalities other than CT, so as used herein the term "view" is not limited to the use described above with respect to projection data from one gantry angle. The term "view" is used to mean one data acquisition whenever there are multiple data acquisitions from different angles, whether from a CT, PET, or SPECT acquisition, and/or any other modality including modalities yet to be developed as well as combinations thereof in fused (e.g., hybrid) embodiments.

The projection data is processed to reconstruct an image that corresponds to a two-dimensional slice taken through the object or, in some examples where the projection data includes multiple views or scans, a three-dimensional rendering of the object. One method for reconstructing an image from a set of projection data is referred to as the FBP technique. Transmission and emission tomography reconstruction techniques also include statistical iterative methods such as the MLEM and ordered-subsets expectation-reconstruction techniques as well as iterative reconstruction techniques. This process converts the attenuation measurements from a scan into integers called "CT numbers" or "Hounsfield units" (HU), which are used to control the brightness (or intensity) of a corresponding pixel on a display device.

To reduce the total scan time, a "helical" scan may be performed. To perform the helical scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, the phrase "reconstructing an image" is not intended to exclude embodiments of the present invention in which data representing an image is generated but a viewable image is not. Therefore, as used herein, the term "image" broadly refers to both viewable images and data representing a viewable image. However, many embodiments generate (or are configured to generate) at least one viewable image.

FIG. 3 illustrates an exemplary imaging system 300 that is similar to the CT system 200 of FIG. 2. In accordance with aspects of the present disclosure, the imaging system 300 is configured for imaging a subject 304 (e.g., the subject 212 of FIG. 2). In one embodiment, the imaging system 300 includes the detector array 208. As such, components of FIG. 3 that function the same as those introduced in FIG. 2 are numbered the same and will not be reintroduced. The detector array 208 further includes a plurality of detector elements 302 that together sense the x-ray radiation beams 206 that pass through the subject 304 (such as a patient) to acquire corresponding projection data. Accordingly, in one embodiment, the detector array 208 is fabricated in a multi-slice configuration including the plurality of rows of cells or detector elements 302. In such a configuration, one or more additional rows of the detector elements 302 are arranged in a parallel configuration for acquiring the projection data.

In certain embodiments, the imaging system 300 is configured to traverse different angular positions around the subject 304 for acquiring desired projection data. Accordingly, the gantry 202 and the components mounted thereon may be configured to rotate about a center of rotation 306 for acquiring the projection data, for example, at different energy levels. Alternatively, in embodiments where a projection angle relative to the subject 304 varies as a function of time, the mounted components may be configured to move along a general curve rather than along a segment of a circle.

As the x-ray source 204 and the detector array 208 rotate, the detector array 208 collects data of the attenuated x-ray beams. The data collected by the detector array 208 undergoes pre-processing and calibration to condition the data to represent the line integrals of the attenuation coefficients of the scanned subject 304. The processed data are commonly called projections. In some examples, the individual detectors or detector elements 302 of the detector array 208 may include photon-counting detectors that register the interactions of individual photons into one or more energy bins. It should be appreciated that the methods described herein may also be implemented with energy-integrating detectors.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the imaging system 300 reveals internal features of the subject 304, expressed in the densities of two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 300 includes a control mechanism 308 to control movement of the components such as rotation of the gantry 202 and the operation of the x-ray source 204. In certain embodiments, the control mechanism 308 further includes an x-ray controller 310 configured to provide power and timing signals to the x-ray source 204. Additionally, the control mechanism 308 includes a gantry motor controller 312 configured to control a rotational speed and/or position of the gantry 202 based on imaging parameters.

In certain embodiments, the control mechanism 308 further includes a data acquisition system (DAS) 314 configured to sample analog data received from the detector elements 302 and convert the analog data to digital signals for subsequent processing. The DAS 314 may be further configured to selectively aggregate analog data from a subset of the detector elements 302 into so-called macro-detectors, as described further herein. The data sampled and digitized by the DAS 314 is transmitted to a computer or computing device 316. In one example, the computing device 316 stores the data in a storage device or mass storage 318. The storage device 318, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 316 provides commands and parameters to one or more of the DAS 314, the x-ray controller 310, and the gantry motor controller 312 for controlling system operations such as data acquisition and/or processing. In certain embodiments, the computing device 316 controls system operations based on operator input. The computing device 316 receives the operator input, for example, including commands and/or scanning parameters via an operator console 320 operatively coupled to the computing device 316. The operator console 320 may include a keyboard (not shown) or a touchscreen, for example, to allow the operator to specify the commands and/or scanning parameters.

Although FIG. 3 illustrates only one operator console 320, more than one operator console may be coupled to the imaging system 300, for example, for inputting or outputting system parameters, requesting examinations, plotting data, and/or viewing images. Further, in certain embodiments, the imaging system 300 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc. For example, imaging system 300 may be coupled to image processing system 100 of FIG. 1.

In one embodiment, for example, the imaging system 300 either includes, or is coupled to, a picture archiving and communications system (PACS) 324. In an exemplary implementation, the PACS 324 is further coupled to a remote system such as a radiology department information system, hospital information system, and/or to an internal or external network (not shown) to allow operators at different locations to supply commands and parameters and/or gain access to the image data.

The computing device 316 uses the operator-supplied and/or system-defined commands and parameters to operate a table motor controller 326, which in turn, may control the table 214, which may be a motorized table. Specifically, the table motor controller 326 may move the table 214 for appropriately positioning the subject 304 in the gantry 202 for acquiring projection data corresponding to the target volume of the subject 304.

As previously noted, the DAS 314 samples and digitizes the projection data acquired by the detector elements 302. Subsequently, an image reconstructor 330 uses the sampled and digitized x-ray data to perform high-speed reconstruction. Although FIG. 3 illustrates the image reconstructor 330 as a separate entity, in certain embodiments, the image reconstructor 330 may form part of the computing device 316. Alternatively, the image reconstructor 330 may be absent from the imaging system 300, and instead the computing device 316 may perform one or more functions of the image reconstructor 330. Moreover, the image reconstructor 330 may be located locally or remotely, and may be operatively connected to the imaging system 300 using a wired or wireless network. Particularly, one exemplary embodiment may use computing resources in a "cloud" network cluster for the image reconstructor 330. Further, in some examples, the image reconstructor 330 is included as a part of image processor unit 210 of FIG. 2.

In one embodiment, the image reconstructor 330 stores the images reconstructed in the storage device 318. Alternatively, the image reconstructor 330 may transmit the reconstructed images to the computing device 316 for generating useful patient information for diagnosis and evaluation. In certain embodiments, the computing device 316 may transmit the reconstructed images and/or the patient information to a display or display device 332 communicatively coupled to the computing device 316 and/or the image reconstructor 330. In one embodiment, the display 332 allows the operator to evaluate the imaged anatomy. The display 332 may also allow the operator to select a volume of interest (VOI) and/or request patient information, for example, via a graphical user interface (GUI) for a subsequent scan or processing.

In some embodiments, the reconstructed images may be transmitted from the computing device 316 or the image reconstructor 330 to the storage device 318 for short-term or long-term storage. Further, in some embodiments, the computing device 316 may be or may be operationally coupled to the processor 104 of FIG. 1. As such, raw data and/or images reconstructed from data acquired by the imaging system 300 may be transmitted to the image processing system 100 (see FIG. 1) for further processing and analysis. Further, the various methods and processes described further herein (such as the methods described below with reference to FIGS. 5 and 6) may be stored as executable instructions in non-transitory memory on a computing device (or controller). At least some of the instructions may be stored in non-transitory memory in imaging system 300. In one embodiment, the image reconstructor 330 may include such executable instructions in non-transitory memory to reconstruct an image from scanning data. In another embodiment, the computing device 316 may include the instructions in non-transitory memory, and may apply the methods described herein, at least in part, to a reconstructed image after receiving the reconstructed image from the image reconstructor 330. In yet another embodiment, the methods and processes described herein may be distributed across the image reconstructor 330 and the computing device 316. Additionally or alternatively, the methods and processes described herein may be distributed across the imaging system 300 (e.g., in the image reconstructor 330 and/or the computing device 316) and the image processing system 100 of FIG. 1 (e.g., in the processor 104 and/or the non-transitory memory 106).

Next, FIG. 4 shows a block diagram of an example workflow 400 for virtual imaging that may be used to produced simulated radiology studies. The workflow 400 may be carried out using the exemplary systems described above, such as the image processing system 100 of FIG. 1 and using images acquired via the systems shown in FIGS. 2 and 3. The simulated radiology studies may provide a user, such as a healthcare provider (e.g., a radiologist or radiology technician) or a vendor, what an image of a patient (e.g., subject) of interest is expected to look like using a particular imaging system and protocol (e.g., an expected or predicted medical image). For example, the user may wish to visualize an image of the patient in a different anatomical or physiological state, such as a state with reduced heart rate or respiration or a state with a planned implant. As another example, the vendor may use the simulated radiology studies to assess whether a prospective product is expected increase image quality or to obtain validation data for regulatory approval of a medical device (e.g., via virtual clinical trials). As yet another example, the simulated radiology studies may help guide imaging protocol selection in order to reduce noise, increase contrast, reduce radiation exposure, or provide other favorable imaging outcomes that increase diagnostic imaging quality while reducing rescans and patient discomfort. As a further example, a vendor may, using images derived from one scanner, simulate the appearance of such images on a second scanner, with the intent to obtain regulatory clearance for the second scanner. For example, an adversarial neural network (e.g., generative adversarial network [GAN]) may be trained to produce images as indistinguishable as possible from true images obtained from the second scanner. The regulatory clearance of the first scanner, together with the simulated images from the second scanner, may form part of the application for regulatory clearance of the second scanner, or both the first and second scanner.

A scan intent 402, patient information 404, and user selections 406 are input into a simulation module 408. As one example, the simulation module 408 may be the simulation module 112 of FIG. 1. One or more of the scan intent 402, the patient information 404, and the user selections 406 may be input via a user input device, such as the user input device 32 of FIG. 1. The scan intent 402 may include, for example, one or more of a diagnostic/interventional intent (e.g., the diagnosis or intervention to be performed via the imaging), a regulatory clearance intent, and a parameter optimization intent. The parameter optimization intent may include one or more of a desire to optimize a contrast injection timing and/or dose; a desire to minimize a radiation dose without unacceptable noise; a desire to optimize image smoothness, contrast, and/or resolution; a desire to observe motion artifacts at various heart rates or respiration rates; a desired to observe different bladder fill or abdominal gas states; a desire to observe an imaging affect from implants or radiofrequency beacons; etc. The user selections 406 may provide further constraints to the virtual imaging. For example, the user selections 406 may specify one or more of a desired imaging modality (e.g., CT, MRI, PET) to be used, a particular scanner model to be used, a particular imaging protocol to be used, an anatomical region to be imaged, a type of contrast agent or radionuclide to be used, and so forth. In some examples, the user may not input the user selections 406 in order to allow the workflow 400 to simulate images with fewer constraints. For example, the workflow 400 may produce simulated images in a plurality of imaging modalities (e.g., both CT images and MR images) when no imaging modality is selected, enabling the user to compare the predicted results from more than one imaging modality. In other examples, the user selections 406 may enable the user to narrow the simulated radiology studies based on available equipment, contrast agents, etc.

The patient information 404 may be at least partially input by the user (e.g., via the user input device) and/or accessed via electronic medical records stored in a networked database. The patient information 404 may include, for example, a size (e.g., height and weight), shape, age, sex, diagnosis, and demographic characteristics (e.g., race) of the patient of interest. The patient information 404 may further include prior images of the patient of interest obtained with any imaging modality. In some embodiments, a (lower quality) scout or preliminary scan of the patient may be performed in order to generally map anatomical features of the patient prior to a (higher quality) diagnostic scan, and the scout scan may be included in the patient information 404 so that the workflow 400 may aid in protocol selection for the diagnostic scan.

The simulation module 408 receives the scan intent 402, the patient information 404, and the user selections 406 and may use various combinations of a style transfer module 410, a digital model building module 412, a simulation framework 414, and an image database 416 to generate more or more simulated images 418 based on the received information. For example, the simulation module 408 may select images from the image database 416 by finding the most similar patients in the database to the patient of interest based on size, shape, demographics, diagnosis, and/or image/medical record similarity. Further, data may be combined from multiple different acquisitions, such as studies performed on multiple different patients and/or acquired using multiple different imaging modalities. The image database 416 may also include digital phantoms (such as those used in virtual clinical trials).

In some embodiments, the image database 416 may include tags associated with each image that can be recalled by the simulation module 408 to aid in image identification. The tags may be manually input by healthcare professionals and/or added by an automated feature that reviews case notes, medical records, and image metadata. The tags may include information regarding patient size, shape, demographics, diagnosis, implant type and location, an imaging modality used to generate the image, a scan protocol used to generate the image, various scan parameters used to generate the image, etc. For example, scan parameters for CT imaging may include an x-ray tube current and peak voltage, a helical pitch, a slice thickness, a spatial resolution, a reconstruction kernel, a reconstruction algorithm used, reconstruction parameters used, a focal spot size, a focal spot shape, a rotation speed, a tube power, a patient table height, a patient table lateral offset, a contrast amount, a contrast injection protocol, a motion correction algorithm used, a detector type (energy integrating/photon counting), a type of contrast agent(s) injected, whether targeted contrast (e.g., gold nanoparticles attached to antibodies) was used, a number of views, a view increment, and a number and thresholds of photon counting energy bins. Planar x-ray imaging may include a portion of the scan parameters for CT imaging, such as the x-ray tube current and peak voltage, the focal spot size and shape, the tube power, etc. As another example, scan parameters for PET or SPECT imaging may include injected isotope(s), an isotope dose, an isotope injection timing, a detector resolution, reconstruction settings, a motion correction algorithm used, a slice thickness, attenuation correction, tracer kinetics, and a rotation speed (e.g., for SPECT). Scan parameters for MR imaging may include, for example, a field strength, a pulse sequence, a coil used, a contrast protocol, a spatial resolution, and a temporal resolution. As yet another example, scan settings for ultrasound may include a pulse sequence, a transducer, a transducer frequency, an insonation angle, Doppler parameters, a gain, a frame rate, a resolution, and whether a microbubble (contrast) protocol was used.

In some embodiments, the user may be presented with one or more of the images identified by the simulation module 408, and the user may input additional user selections 406 to choose or refine the images to be selected in order to better match the target case. For example, if a lower radiation dose is to be given, image noise may be adjusted accordingly. Metal implants may be added to match specifics of the patient of interest. As another example, a state of fill of organs such as the bladder may be adjusted.

The image(s) selected by the simulation module 408, the user, and/or input with the patient information 404 may be processed via one or any combination of the style transfer module 410, the digital model building module 412, and the simulation framework 414. The style transfer module 410 may perform style transfer between the modality/protocol of the selected image(s) to the desired modality/protocol, when specified, or to a plurality of modality/protocol options. For example, an MR image series may be used to generate a CT image using a style transfer model. The style transfer model may use neural network architectures, such as generative adversarial networks, and/or physics/anatomic/physiological simulation to generate images of a first type of imaging (e.g., a first imaging modality and/or first imaging protocol) from images obtained using a second type of imaging (e.g., a second imaging modality and/or second imaging protocol). Alternatively, the style transfer module 410 may not be used when the selected images were acquired with the same modality/protocol as the desired modality/protocol.

Additionally or alternatively, the digital model building module 412 may use the selected image(s) to build a digital model of the patient of interest. For example, the digital model may be a three-dimensional (3D) anatomical representation of the patient that includes physiological functions and states. For example, the digital model may include a beating heart and respiration, the rates of which may be adjusted by the user, if desired. As another example, organ fill states (e.g., a bladder fill state) may be adjusted by the user. Further, when specified, implants or radiofrequency (RF) beacons may be included in the digital model. The simulation framework 414 simulates operation of an imaging system based on the input scan intent 402 and the user selections 406, when included, to virtually image the digital model of the patient of interest. For example, the simulation framework 414 may use physics of the acquisition process and how it interacts with the human body, as specified by the anatomy and physiology digital model, and any implants or RF beacons present. The simulation framework 414 may use Monte Carlo methods, other radiation transport models, or approximations thereof (e.g., for x-ray and nuclear imaging) to produce the one or more simulated images 418. The one or more simulated images 418 may include images generated for multiple dose levels (by using, for example, Monte Carlo generated images at various points in the simulation), multiple energies (e.g., by selecting Monte Carlo events by energy so as to match the distribution of each input spectrum used to simulate an image), multiple imaging modalities, and so forth.

The one or more simulated images 418 may be output to the user via a display device, such as the display device 33 of FIG. 1. In some examples, the user may provide additional user selections 406 to refine the one or more simulated images 418. For example, the user may change a dose level, a contrast agent injection timing, etc., and the simulation module 408 may re-simulate the one or more simulated images 418 based on the additional user selections 406 or use interpolation/extrapolation to adjust the one or more simulated images 418. Further, the user may select one of the simulated image(s) to receive an imaging protocol 420 associated with the selected simulated image. For example, the user may select the simulated image having a highest signal-to-noise ratio, a highest contrast, or having another desired imaging result. The imaging protocol 420 may include the imaging parameters used by the simulation framework 414 in generating the corresponding simulated image 418. For example, the imaging protocol 420 may be displayed via the display device. In some embodiments, the imaging protocol 420 may be retrievable or pre-loaded within a scan acquisition program so that the user may acquire actual images of the patient of interest using the imaging protocol 420 of the selected simulated image, enabling faster imaging with fewer manual inputs.

As used herein, the term "virtual" denotes processes that are not physically performed but performed by software. For example, "virtual imaging" describes the process of the simulation framework 414 modeling an image acquisition process as specified by a virtual imaging protocol. Similarly, the "virtual imaging protocol" is not physically performed by imaging system hardware (e.g., the x-ray source 204 and the detector array 208), but the virtually imaging protocol may be output as executable instructions for physically performing an image acquisition via the imaging system (e.g., as the imaging protocol 420).

Turning now to FIG. 5, a flow chart of an exemplary method 500 for simulating medical images is shown. The method 500 and the rest of the methods included herein may be performed by one or more processors, such as the processor 104 of FIG. 1, based on instructions stored in one or more memories, such as the simulation module 112 of the non-transitory memory 106 of FIG. 1, and inputs received from a user (e.g., via the user input device 32 of FIG. 1). For example, the method 500 may be used to implement the workflow 400 of FIG. 4.

At 502, the method 500 includes receiving a scan intent, patient information, and user selections for virtual imaging. The user may input the scan intent, the patient information, and the user selections via the user interface, which may be operably coupled to the one or more processors. As described above with respect to FIG. 4, the scan intent may include, for example, a diagnostic/interventional task to be performed. For example, the diagnostic intent may include a type of diagnosis (e.g., to look for trauma or a disease state), and the interventional task may include a type of procedure to be performed (such as catheter insertion, artery mapping, a type of surgery, etc.). Additionally or alternatively, the scan intent may include a parameter optimization intent, such as optimization of an injection timing of a contrast agent or isotope (e.g., radionuclide tracer, radionuclide-attached antibody), optimization of a dose of the contrast agent or isotope, optimization of a radiation dose, optimization of an image smoothness, optimization of an image contrast, optimization of an image resolution, optimization of motion artifacts, optimization of organ fill states, and/or optimization of implant or RF beacon imaging.

The user selections may specify at least one of an imaging modality to be used (e.g., CT, MRI, PET), particular equipment (e.g., a specific scanner model) to be used, a particular imaging protocol to be used, an anatomical region to be imaged, a type of contrast agent or radionuclide tracer to be used, and so forth. In some examples, the user may not include specific user selections to enable the method 500 to generate a wider variety of simulated images, such as images of different imaging modalities, different imaging protocols, etc. In contrast, the user selections may enable the user to avoid simulating images using modalities or protocols that are not available for use or contraindicated.

The patient information may include a size, shape, age, sex, diagnosis, and demographic characteristics (e.g., race), and previous acquired medical images of the patient. Additionally or alternatively, the user may input patient identifying information, such as a name and date of birth or a patient identification number, and the processor may retrieve additional patient information from an electronic medical record of the patient.

At 504, the method 500 includes selecting images to use for the virtual imaging from an image database based on the received scan intent, the received patient information, and the received user selections. The images to use for the virtual imaging comprise one or more previously obtained (e.g., prior) medical images of the patient, one or more previously obtained medical images of one or a plurality of different patients selected to match demographics of the patient, and/or one or more previously generated images of digital phantoms. The previously obtained medical images, whether of the same patient or different patients, may comprise images obtained over a plurality of image acquisitions using one or a plurality of different imaging modalities and protocols. For example, the selected images may include a first image of a first different patient acquired using a CT system, a second image of a second different patient acquired using an MRI system, and a third image of a third different patient acquired using a different CT system and protocol.

In some embodiments, selecting the images to use for the virtual imaging further includes displaying potential images and refining the image selection based on user input, as optionally indicated at 506. For example, the user may review the potential images, selected by the processor based on the demographics of the patient to be virtually imaged, and confirm or reject inclusion of each of the potential images for building a virtual model of the patient (e.g., at 508). As an illustrative example, the user may select a previously obtained medical image that includes an implant in a similar location to the patient to be virtually imaged. As another illustrative example, the user may reject a previously obtained medical image that includes poor contrast or high noise.

At 508, the method 500 includes building a digital model of the patient based on the selected images. The digital model of the patient comprises a 3D anatomical representation of the patient and includes physiological functions, such as breathing. As a result, motion artifacts due to different respiration rates or different heart rates may be assessed via the virtual imaging, when desired (e.g., as specified via the scan intent and/or the user selections received at 502). In some examples, the digital model may include a partial anatomical representation of the patient instead of a whole-body representation, such as when the virtual imaging is constrained to a particular anatomical location. As a non-limiting example, when images of the heart are desired (e.g., as specified via the scan intent and/or the user selections), the digital model may include an upper torso of the patient and may not include limbs, the head, and other anatomical regions that are not part of the upper torso.

As another non-limiting example, when images of the brain are desired, the digital model may include the head only.

At 510, the method 500 includes virtually imaging the digital model to generate one or more simulated images based on the scan intent and the user selections. The simulated images comprise predicted medical images of the patient using a defined imaging system and scan parameters. For example, the processor may generate a virtual imaging (e.g., scan) protocol based on the scan intent and the user selections and generate the one or more simulated images based on physics of an image acquisition process according to the virtual imaging protocol. A sub-set of data from the digital model of the patient may be processed, such as according to a slice location and thickness specified by the virtual imaging protocol.

In some examples, the virtual imaging protocol may be adjusted to produce different simulated images. For example, adjusting the virtual imaging protocol may include generating a different virtual protocol for each different imaging modality. As another example, adjusting the virtual protocol may include adjusting one or more scan parameters for a same imaging modality. As an illustrative example, a first simulated CT image may be generated via a first virtual protocol that includes a first spatial resolution, and a second simulated CT image may be generated via a second virtual protocol that includes a second spatial resolution. Further, multiple simulated images may be generated using a same virtual protocol but with adjusted physiological states of the patient. As an illustrative example, a first simulated image may be generated for a first, faster heart rate, and a second simulated image may be generated for a second, slower heart rate using the same virtual protocol in order to assess how heart rate affects image quality. As still another example, the same virtual protocol may be used for different scanners of a same imaging modality in order to assess a difference in image quality between the different scanners. Thus, a plurality of different simulated images may be generated using the same or different virtual protocol for the same or different physiological state of the patient.

Virtually imaging the digital model optionally includes performing style transfer on the selected images based on the desired imaging modality and/or protocol, as indicated at 512. Continuing the example given above at 504, the processor may convert the second (MR) image to a CT image style when the desired imaging modality is CT. As described with respect to FIG. 4, the style transfer may include using neural network architectures, such as generative adversarial networks, and/or physics/anatomic/physiological simulation to convert an image of a first imaging modality or protocol to a style of a second imaging modality or protocol. While images may be synthesized from the digital model alone in some cases, it may be difficult because some parameters are not known. For example, MR images have different contrast mechanisms depending on pulse sequence, and so it may be difficult to synthesize CT images from some MR images without learning how various tissues map between modalities (e.g. a $T_2$ MR image to a 120 kVp CT image) from prior imaging studies using this pair of acquisitions. As such, performing the style transfer may include using known tissue contrast mapping between imaging modalities in simulating the images.

At 514, the method 500 includes displaying the one or more simulated images. For example, the one or more simulated images may be output to a display, such as the display device 33 of FIG. 1. The one or more simulated images may be displayed in a tiled format so that the user may observe more than one simulated image at once. Additionally or alternatively, the user may select which image to observe in an isolated (e.g., fullscreen) view.

At 516, the method 500 includes receiving a user selection of one simulated image. For example, the user may select a most desirable simulated image. The user may select the one simulated image using the user input device, for example. In some embodiments, the simulated images that are not selected may be stored, at least temporarily, so that the user (or another clinician) may review the unselected simulated images at a later time. As another example, the user may initially select a first simulated image and then select a second simulated image at a later time (e.g., minutes, hours, days, weeks, months, or years later). For example, the simulated images may be stored in the electronic medical record of the patient.

At 518, the method 500 includes outputting an imaging protocol for the selected simulated image. The imaging protocol may include the parameters used in the virtual imaging, including the imaging modality, particular equipment, patient physiological state, and scan parameters used in the modeling of the image acquisition process (e.g., as defined by the virtual imaging protocol). Thus, the imaging protocol, which may be used for a physical image acquisition, may be generated based on the virtual imaging protocol. As an illustrative example, for a CT imaging modality, the output imaging protocol may specify a particular CT scanner, an x-ray tube current and peak voltage, a helical pitch, a slice thickness, a spatial resolution, a rotation speed of a gantry, a tube power, a patient table height, a patient table lateral offset, a contrast amount, a contrast injection protocol, a number of views to acquire, a view increment, a reconstruction kernel to use following image data acquisition, a reconstruction algorithm to use following the image data acquisition, reconstruction parameters to use following the image data acquisition, and a motion correction to use following the image data acquisition.

As mentioned above, the user may subsequently select a different simulated image (e.g., the second simulated image), and thus, the imaging protocol may be output for the second simulated image upon selection of the second simulated image without repeating the virtual imaging.

At 520, the method 500 optionally includes performing imaging of the patient using the output imaging protocol. As will be elaborated below with respect to FIG. 6, the imaging protocol may be directly output to an image acquisition system to prepare for physically imaging the patient. As another example, additionally or alternatively, outputting the imaging protocol may include saving the imaging protocol in a format that is readable by the image acquisition system so that the user may select and load the imaging protocol when patient imaging is desired. The method 500 may then return.

Figure 6:
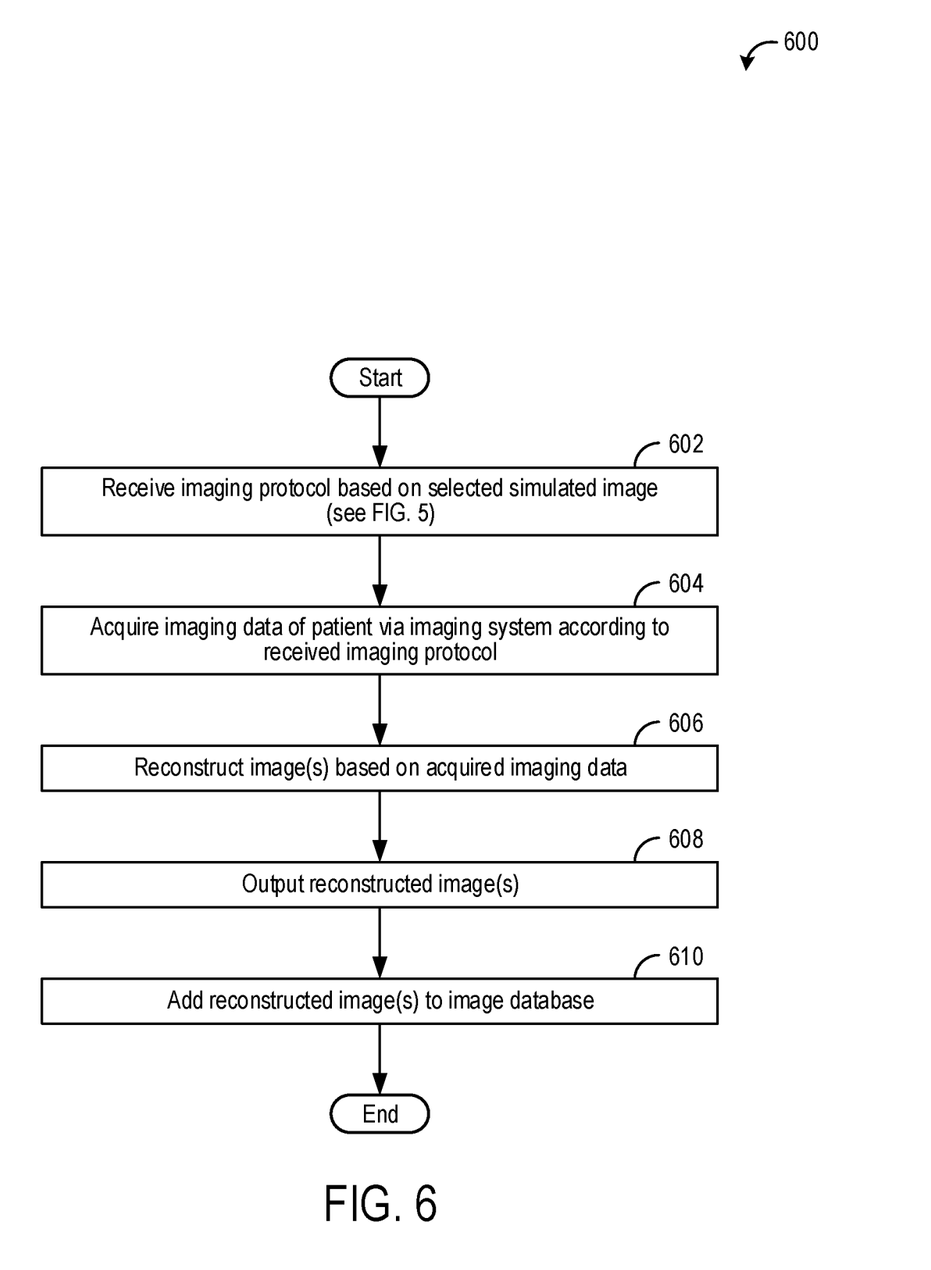
FIG. 6 is a flow chart of an exemplary method for acquiring medical images of a patient using a protocol developed via virtual imaging, according to an embodiment.

Continuing to FIG. 6, and example method 600 is provided for imaging a patient using an imaging protocol developed via a simulated radiology study of the patient. The method 600 may be performed by one or more computing devices, such as the computing device 316 of FIG. 3, based on instructions stored in one or more memories and inputs received from a user (e.g., via the operator console 320 of FIG. 3). In some embodiments, the method 600 may be performed as a part of the method 500 of FIG. 5 (e.g., at 520). Further, the method 600 may be performed using an imaging system. Although the method 600 will be described with respect to a CT system, it may be understood that method 600 may be adapted to any medical imaging system without departing from the scope of this disclosure.

At 602, the method 600 includes receiving an imaging protocol based on a selected simulated image, as described above with respect to FIG. 5. Thus, the imaging protocol may define settings for acquiring imaging data in order to replicate or approximate the predicted images of the virtual imaging. The imaging protocol may include, for example, an x-ray tube current and peak voltage, a helical pitch, a slice thickness, a spatial resolution, a rotation speed of a gantry, a tube power, a start scan position (including a patient table height and lateral offset), an end scan position, a contrast amount, a contrast injection protocol, a number of views to acquire, a view increment, a reconstruction kernel to use following image data acquisition, a reconstruction algorithm to use following the image data acquisition, reconstruction parameters to use following the image data acquisition, and a motion correction to use following the image data acquisition.

At 604, the method 600 includes acquiring imaging data of the patient via the imaging system according to the received imaging protocol. For example, the imaging data may be acquired for a diagnostic scan of the patient. The diagnostic scan may be initiated by the user by inputting a start command at the operator console. Alternatively, the diagnostic scan may be automatically initiated responsive to the patient table reaching the desired height and lateral offset for the start scan position. During the diagnostic scan, an x-ray source (e.g., the x-ray tube) is activated according to the parameters specified by the imaging protocol (e.g., at a specified kV, mA, attenuation filter position), and the rotation of the gantry is controlled to achieve the scan angles specified by the received imaging protocol. Further, during the scan, the position of the patient table may be moved such that the scan progresses from the start scan location to the stop scan location.

At 606, the method 600 includes reconstructing image(s) based on the acquired imaging data. The one or more images may be reconstructed using, as a non-limiting example, an analytic reconstruction algorithm, such as filtered backprojection or an iterative reconstruction algorithm. Further, the reconstruction algorithm used may be specified by the received imaging protocol. Further, motion correction algorithms or other corrective algorithms may be performed according to the received imaging protocol.

At 608, the method 600 includes outputting the reconstructed image(s). For example, the one or more images may be output to a display device, such as display 332 of FIG. 3. In this way, the user of the imaging system may review the image(s). As another example, outputting the reconstructed image(s) may include saving the images, such as to a picture archiving system (e.g., PACS 324 of FIG. 3). Additionally or alternatively, outputting the reconstructed image(s) may include saving the one or more reconstructed images to the patient's electronic medical record.

At 610, the method 600 includes adding the reconstructed image(s) to an image database. The image database may be the image database 416 of FIG. 4, for example, so that the reconstructed image(s) may be used in simulating medical images during subsequent virtual imaging studies. Further, as described with respect to FIG. 4, the reconstructed images may be stored with descriptive tags to aid in image retrieval. The method 600 may then end.

In this way, medical imaging may be performed with more optimal use of a particular imaging system for a specific diagnostic or interventional task by using the simulated radiology studies to optimize image acquisition settings. As a result, an occurrence of suboptimal or unusable studies may be reduced, thereby increasing an imaging throughput and reducing a provider burden. Further, user training on new protocols and imaging equipment may be accelerated. Further still, patient comfort may be increased by reducing a dose of radiation, a dose of contrast, and/or a dose of radiotracer used. Reducing a number of repeat scans may further increase patient comfort and satisfaction.

A technical effect of acquiring imaging data using a protocol generated via simulated radiology studies is that a resulting image quality may be increased while imaging throughput is also increased.

The disclosure also provides support for a method, comprising: generating a simulated medical image of a patient via virtual imaging based on previously obtained medical images and a scan intent of the virtual imaging, and outputting an imaging protocol based on a virtual protocol of the virtual imaging. In a first example of the method, the previously obtained medical images comprise one or more of previously obtained medical images of the patient and previously obtained medical images of different patients selected to match demographics of the patient. In a second example of the method, optionally including the first example, the previously obtained medical images are obtained via a first type of imaging and the scan intent of the virtual imaging includes using a second type of imaging, and the method further comprises performing style transfer on the previously obtained medical images to simulate obtaining the previously obtained medical images using the second type of imaging. In a third example of the method, optionally including one or both of the first and second examples, the first type of imaging and the second type of imaging include different imaging modalities. In a fourth example of the method, optionally including one or more or each of the first through third examples, the first type of imaging and the second type of imaging include different imaging protocols. In a fifth example of the method, optionally including one or more or each of the first through fourth examples, performing the style transfer comprises processing the previously obtained medical images via one or more of a generative adversarial network, a physics simulation, an anatomic simulation, and a physiological simulation. In a sixth example of the method, optionally including one or more or each of the first through fifth examples, generating the simulated medical image of the patient via the virtual imaging based on the previously obtained medical images and the scan intent of the virtual imaging comprises: building a digital model of the patient based on the previously obtained medical images, generating the virtual protocol for the virtual imaging based on the scan intent of the virtual imaging, and virtually imaging the digital model of the patient using the virtual protocol. In a seventh example of the method, optionally including one or more or each of the first through sixth examples, the virtual imaging uses one or more of a Monte Carlo method and a radiation transport model. In an eighth example of the method, optionally including one or more or each of the first through seventh examples, generating the virtual protocol for the virtual imaging is further based on a user selection, the user selection comprising one or more of a desired imaging modality, a desired imaging protocol, a desired imaging system model, a type of contrast agent, a type of radionuclide. In a ninth example of the method, optionally including one or more or each of the first through eighth examples, the scan intent comprises one or more of a diagnostic intent, an interventional intent, a regulatory clearance intent, and a parameter optimization intent. In a tenth example of the method, optionally including one or more or each of the first through ninth examples, the parameter optimization intent comprises one or more of optimization of an injection timing of a contrast agent, optimization of a dose of the contrast agent, optimization of a radiation dose, optimization of an image smoothness, optimization of an image contrast, optimization of an image resolution, optimization of motion artifacts, optimization of organ fill states, and optimization of implant imaging.

The disclosure also provides support for a method, comprising: selecting one or more previously obtained medical images based on demographics of a patient, building a three-dimensional (3D) anatomical representation of the patient using the one or more previously obtained medical images, and generating an expected medical image of the patient by processing the 3D anatomical representation of the patient using physics of an image acquisition process and a protocol generated based on an imaging intent and user selections. In a first example of the method, the one or more previously obtained medical images comprise at least one of prior medical images of the patient, prior medical images of one or a plurality of other patients, and medical images of digital phantoms. In a second example of the method, optionally including the first example, selecting the one or more previously obtained medical images comprises: outputting a plurality of potential medical images to a display, the plurality of potential medical images selected from an image database according to the demographics of the patient, and selecting the one or more previously obtained medical images from the plurality of potential medical images based on user input. In a third example of the method, optionally including one or both of the first and second examples, the imaging intent and the user selections provide constraints for the image acquisition process, including at least one of an imaging modality of the image acquisition process, a diagnostic intent of the image acquisition process, a type of contrast agent for the image acquisition process, a type of radionuclide for the image acquisition process, contrast optimization for the image acquisition process, dose optimization for the image acquisition process, and timing optimization for the image acquisition process. In a fourth example of the method, optionally including one or more or each of the first through third examples, the method further comprises: generating an imaging protocol for imaging the patient via an imaging system based on the protocol used for generating the expected medical image, acquire imaging data of the patient via the imaging system according to the generated imaging protocol, reconstruct one or more images of the patient based on the acquired imaging data, and output the one or more reconstructed images.

The disclosure also provides support for a system, comprising: a display, and an image processing device operably coupled to the display and storing instructions executable to: retrieve one or more medical images from an image database based on demographic information of a patient, build a three-dimensional (3D) anatomical representation of the patient from the one or more medical images, generate predicted medical images of the patient by processing the 3D anatomical representation of the patient based on physics of an image acquisition process, and output the predicted medical images of the patient to the display. In a first example of the system, the system further comprises: a user interface operatively coupled to the image processing device, and wherein the image processing device stores further instructions executable to: generate a protocol for processing the 3D anatomical representation based on input received via the user interface. In a second example of the system, optionally including the first example, the image processing device stores further instructions executable to: generate an imaging protocol for imaging the patient with an imaging system based on the protocol for processing the 3D anatomical representation, and output the imaging protocol to the imaging system. In a third example of the system, optionally including one or both of the first and second examples, the image database comprises a plurality of medical images acquired over a plurality of different image acquisitions using a plurality of different imaging modalities.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
   generating a simulated medical image of a patient via virtual imaging based on previously obtained medical images and a scan intent of the virtual imaging, wherein the scan intent comprises one or more of an interventional intent, a regulatory clearance intent, and a parameter optimization intent; and
   outputting an imaging protocol based on a virtual protocol of the virtual imaging.

2. The method of claim 1, wherein the previously obtained medical images comprise one or more of previously obtained medical images of the patient and previously obtained medical images of different patients selected to match demographics of the patient.

3. The method of claim 1, wherein the previously obtained medical images are obtained via a first type of imaging and the scan intent of the virtual imaging includes using a second type of imaging, and the method further comprises performing style transfer on the previously obtained medical images to simulate obtaining the previously obtained medical images using the second type of imaging.

4. The method of claim 3, wherein the first type of imaging and the second type of imaging include different imaging modalities.

5. The method of claim 3, wherein the first type of imaging and the second type of imaging include different imaging protocols.

6. The method of claim 3, wherein performing the style transfer comprises processing the previously obtained medical images via one or more of a generative adversarial network and a physiological simulation.

7. The method of claim 1, wherein generating the simulated medical image of the patient via the virtual imaging based on the previously obtained medical images and the scan intent of the virtual imaging comprises:
building a digital model of the patient based on the previously obtained medical images;
generating the virtual protocol for the virtual imaging based on the scan intent of the virtual imaging; and
virtually imaging the digital model of the patient using the virtual protocol.

8. The method of claim 7, wherein the virtual imaging uses a Monte Carlo method.

9. The method of claim 7, wherein generating the virtual protocol for the virtual imaging is further based on a user selection, the user selection comprising one or more of a desired imaging system model, a type of contrast agent, and a type of radionuclide.

10. The method of claim 1, wherein the parameter optimization intent comprises one or more of optimization of a dose of a contrast agent, optimization of a radiation dose, optimization of an image smoothness, optimization of an image contrast, optimization of organ fill states, and optimization of implant imaging.

11. A method, comprising:
selecting one or more previously obtained medical images based on demographics of a patient;
building a three-dimensional (3D) anatomical representation of the patient using the one or more previously obtained medical images; and
generating an expected medical image of the patient by processing the 3D anatomical representation of the patient using physics of an image acquisition process and a protocol generated based on an imaging intent and user selections, wherein the imaging intent comprises one or more of an interventional intent, a regulatory clearance intent, and a parameter optimization intent.

12. The method of claim 11, wherein the one or more previously obtained medical images comprise medical images of digital phantoms.

13. The method of claim 11, wherein selecting the one or more previously obtained medical images comprises:
outputting a plurality of potential medical images to a display, the plurality of potential medical images selected from an image database according to the demographics of the patient; and
selecting the one or more previously obtained medical images from the plurality of potential medical images based on user input.

14. The method of claim 11, wherein the imaging intent and the user selections provide constraints for the image acquisition process, including at least one of a type of contrast agent for the image acquisition process, a type of radionuclide for the image acquisition process, contrast optimization for the image acquisition process, dose optimization for the image acquisition process, and timing optimization for the image acquisition process.

15. The method of claim 11, further comprising:
generating an imaging protocol for imaging the patient via an imaging system based on the protocol used for generating the expected medical image;
acquire imaging data of the patient via the imaging system according to the generated imaging protocol;
reconstruct one or more images of the patient based on the acquired imaging data; and
output the one or more reconstructed images.

16. A system, comprising:
a display; and
an image processing device operably coupled to the display and storing instructions executable to:
retrieve one or more medical images from an image database based on demographic information of a patient;
build a three-dimensional (3D) anatomical representation of the patient from the one or more medical images;
generate predicted medical images of the patient by processing the 3D anatomical representation of the patient based on physics of an image acquisition process and a protocol generated based on an imaging intent and user selections, wherein the imaging intent comprises one or more of an interventional intent, a regulatory clearance intent, and a parameter optimization intent; and
output the predicted medical images of the patient to the display.

17. The system of claim 16, further comprising a user interface operatively coupled to the image processing device, and wherein the image processing device stores further instructions executable to:
generate a protocol for processing the 3D anatomical representation based on input received via the user interface.

18. The system of claim 17, wherein the image processing device stores further instructions executable to:
generate an imaging protocol for imaging the patient with an imaging system based on the protocol for processing the 3D anatomical representation; and
output the imaging protocol to the imaging system.

19. The system of claim 16, wherein the image database comprises a plurality of medical images acquired over a plurality of different image acquisitions using a plurality of different imaging modalities.

* * * * *